(12) United States Patent
Chen

(10) Patent No.: US 10,195,370 B2
(45) Date of Patent: Feb. 5, 2019

(54) ELECTRONIC CIGARETTE

(71) Applicant: SHENZHEN SMOORE TECHNOLOGY LIMITED, Shenzhen (CN)

(72) Inventor: Zhiping Chen, Shenzhen (CN)

(73) Assignee: SHENZHEN SMOORE TECHNOLOGY LIMITED, Shenzhen (CN)

(*) Notice: Subject to any disclaimer, the term of this patent is extended or adjusted under 35 U.S.C. 154(b) by 0 days.

(21) Appl. No.: 15/517,196

(22) PCT Filed: Jul. 9, 2015

(86) PCT No.: PCT/CN2015/083652
§ 371 (c)(1),
(2) Date: Apr. 6, 2017

(87) PCT Pub. No.: WO2016/065926
PCT Pub. Date: May 6, 2016

(65) Prior Publication Data
US 2017/0303596 A1    Oct. 26, 2017

(30) Foreign Application Priority Data

Oct. 29, 2014  (CN) .......................... 2014 1 0597265

(51) Int. Cl.
*A24F 47/00*   (2006.01)
*A61M 11/04*   (2006.01)
(Continued)

(52) U.S. Cl.
CPC ........... *A61M 11/04* (2013.01); *A24F 47/008* (2013.01); *A61M 11/042* (2014.02);
(Continued)

(58) Field of Classification Search
CPC ..................................................... A24F 47/008
See application file for complete search history.

(56) References Cited

U.S. PATENT DOCUMENTS 8,499,766 B1    8/2013  Newton
9,956,357 B2 *  5/2018  Chen ....................... A61M 11/04
(Continued)

FOREIGN PATENT DOCUMENTS

CN   101528549 A   9/2009
CN   102970885 A   3/2013
(Continued)

OTHER PUBLICATIONS

SIPO, "International Search Report for related application PCT/CN2015/083652", dated Sep. 2, 2015, CN (4 Pages).
(Continued)

*Primary Examiner* — James Harvey
(74) *Attorney, Agent, or Firm* — Mark Malek; Widerman Malek PL

(57) ABSTRACT

An electronic cigarette (10), comprising an atomizing assembly (100) and a power supply assembly (300) connected in a detachable mode; the atomizing assembly (100) comprises a housing (120) and an atomizer (140) located in the housing (120); the housing (120) is provided with an abutment portion (160) therein; the atomizer (140) comprises a reservoir (142) and an atomizing element connected to the reservoir (142); the power supply assembly (300) comprises a first connecting portion (320) facing the atomizer (140); one end of the housing (120) facing the power source assembly (300) is provided with a second connecting portion (180) connected to the first connecting portion (320) in a detachable mode; one end of the atomizer (140) facing the power supply assembly (300) is provided with a third connecting portion (144); and when the first connecting portion (320) is connected to and fixed with the second (Continued)

connecting portion (180), the abutment portion (160) presses the atomizer (140) to enable the third connecting portion (144) to press against the first connecting portion (320).

20 Claims, 12 Drawing Sheets

(51) Int. Cl.
*A61M 15/00* (2006.01)
*A61M 15/06* (2006.01)
*A61M 16/14* (2006.01)

(52) U.S. Cl.
CPC ........ *A61M 15/0021* (2014.02); *A61M 15/06* (2013.01); *A61M 16/142* (2014.02); *A61M 2205/82* (2013.01); *A61M 2205/8206* (2013.01)

(56) References Cited

U.S. PATENT DOCUMENTS

| | | | |
|---|---|---|---|
| 2014/0261486 A1 | 9/2014 | Potter et al. | |
| 2014/0283823 A1 | 9/2014 | Liu | |
| 2016/0338405 A1* | 11/2016 | Liu | A24F 47/008 |
| 2016/0338411 A1* | 11/2016 | Liu | A24F 47/008 |
| 2017/0303596 A1* | 10/2017 | Chen | A24F 47/008 |

FOREIGN PATENT DOCUMENTS

| | | |
|---|---|---|
| CN | 103237470 A | 8/2013 |
| CN | 203353683 U | 12/2013 |
| CN | 103879939 A | 6/2014 |
| CN | 203692550 U | 7/2014 |
| CN | 103960781 A | 8/2014 |
| CN | 104055223 A | 9/2014 |
| CN | 104366695 A | 2/2015 |
| CN | 204245152 U | 4/2015 |
| CN | 202618275 U | 12/2015 |
| WO | WO2014146232 A1 | 9/2014 |

OTHER PUBLICATIONS

SIPO, "International Search Report for related application PCT/CN2015/083652", dated Sep. 2, 2015, EN (2 Pages).
SIPO, "Written Opinion for related application PCT/CN2015/083652", dated Sep. 2, 2015, CN (4 Pages).
SIPO, "Written Opinion for related application PCT/CN2015/083652", dated Sep. 2, 2015, EN (6 Pages).
SIPO, (Office Action for related application CN 201410597265.4, dated Jul. 5, 2016, CN (11 Pages).
SIPO, (Office Action for related application CN 201410597265.4, dated Nov. 30, 2016, CN (8 Pages).
SIPO, (Office Action for related application CN 201410597265.4, dated Apr. 1, 2017, CN (8 Pages).

* cited by examiner

ELECTRONIC CIGARETTE

CROSS-REFERENCE TO RELATED APPLICATIONS

This application claims the benefit of Chinese Patent Application No. 201410597265.4, filed on Oct. 29, 2014, which is hereby incorporated herein by reference in its entirety.

The present disclosure relates to cigarette substitutes, and more particularly relates to an electronic cigarette.

BACKGROUND OF THE INVENTION

Electronic cigarettes include disposable electronic cigarettes and rechargeable electronic cigarettes. In the disposable electronic cigarette, the battery and the atomizer are both located m integral electronic cigarette housing. While the rechargeable electronic cigarette generally includes a battery assembly and an atomizing assembly, which are detachable. The current rechargeable electronic cigarette includes two types, the first is a liquid refillable type, i.e., after the liquid is exhausted, one can add the liquid directly into the atomizing assembly, the second is an atomizing assembly replaceable type, i.e., after the liquid in the atomizing assembly is exhausted, the atomizing assembly can be replaced directly.

According to the first type of rechargeable electronic cigarette, the atomizing assembly can be repeatedly used, therefore, even if the appearance of the atomizing assembly can be made exquisite, it does not increase the cost of the user. However, the problem with this type of electronic cigarette is that, it is inconvenient for the user to refill the liquid, and direct exposure to liquid may cause a security risk. According to the second type of rechargeable electronic cigarette, since the atomizing assembly thereof is disposable, the appearance of the atomizing assembly cannot be made exquisite, otherwise the cost of use will be relatively high.

SUMMARY OF THE INVENTION

Accordingly, it is necessary to provide an electronic cigarette, which has a convenient operation, a low cost of use, and a fine appearance.

An electronic cigarette includes: an atomizing assembly comprising a housing and an atomizer located in the housing; the housing having an abutment portion; the atomizer comprising a reservoir and an atomizing element connected to the reservoir; and a power supply assembly removably connected to the atomizing assembly; the power supply assembly comprising a first connecting portion facing the atomizing assembly; wherein the housing is provided with a second connecting portion on an end thereof facing the power supply assembly, the second connecting portion is removably connected to the first connecting portion; the atomizer is provided with a third connecting portion on an end thereof lacing the power supply assembly; when the first connecting portion is fixedly connected to the second connecting portion, the abutment portion abuts against the atomizer, such that the third connecting portion abuts against the first connecting portion.

According to the foregoing electronic cigarette, when replacing or assembling the atomizer, the atomizer is firstly mounted in the housing, the abutment portion abuts against the atomizer, the power supply assembly is then connected to the housing, the first connecting portion is connected to the second connecting portion, at that time the third connecting portion abuts against the first connecting portion, thus fixing the atomizer in the housing. Thus it is easy for the user to replace or assemble the atomizer of the foregoing electronic cigarette. Since the replaceable atomizer is located in the housing, and the housing is a reusable part, the electronic cigarette has a line appearance, as well as a low cost of use.

BRIEF DESCRIPTION OF THE DRAWINGS

To illustrate the technical solutions according to the embodiments of the present invention or in the prior art more clearly, the accompanying drawings for describing the embodiments or the prior art are introduced briefly is the following. Apparently, the accompanying drawings in the following description are only some embodiments of the present invention, and persons of ordinary skill in the art can derive other drawings from the accompanying drawings without creative efforts.

DETAILED DESCRIPTION OF THE EMBODIMENTS

Reference will now be made to the drawings to describe, in detail, embodiments of the present electronic cigarette. It will be understood that the particular method and device embodying the invention are shown by way of illustration and not as a limitation of the invention. The principles and features of this invention may be employed in various and numerous embodiments without departing from the scope of the invention.

Figure 1:
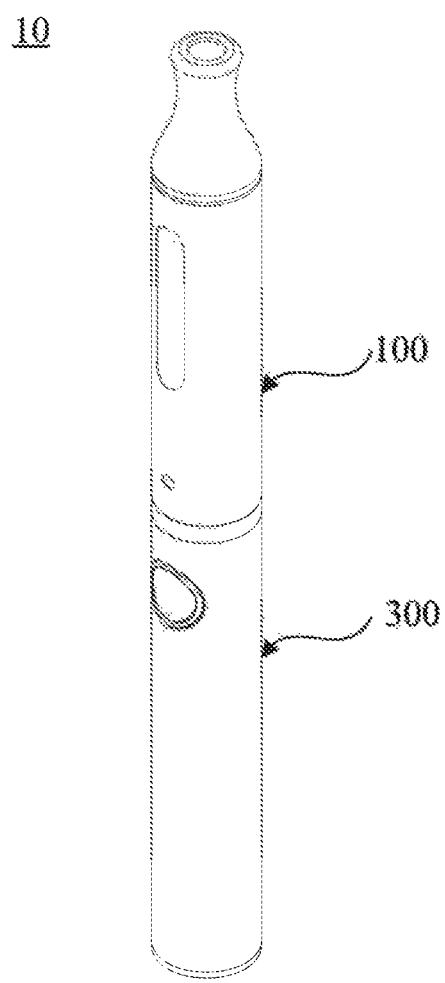
FIG. 1 is a perspective view of an electronic cigarette according to one embodiment.
Figure 2:
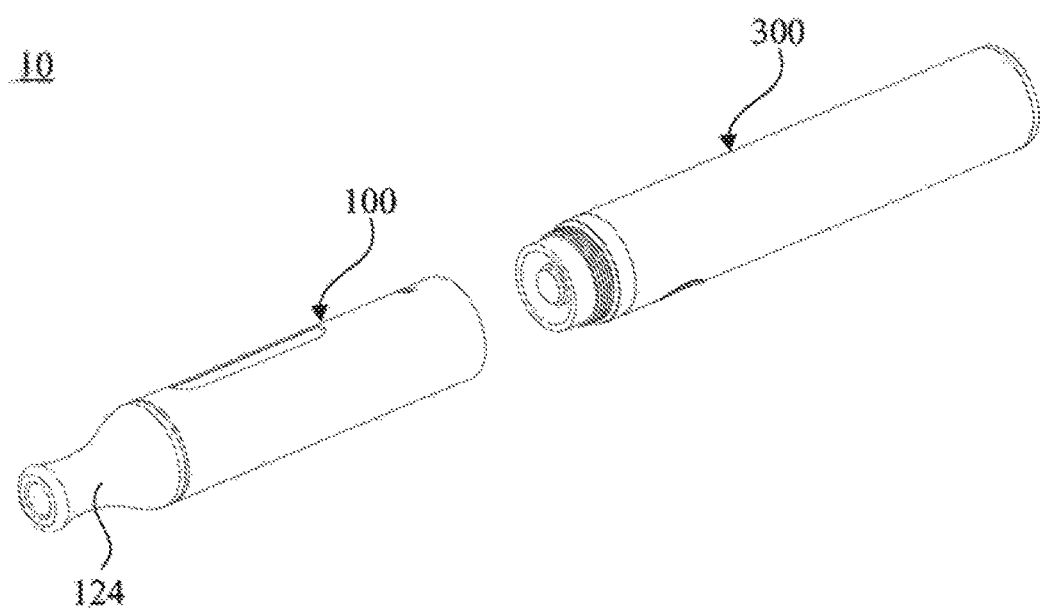
FIG. 2 is an exploded view of the electronic cigarette of FIG. 1.
Figure 3:
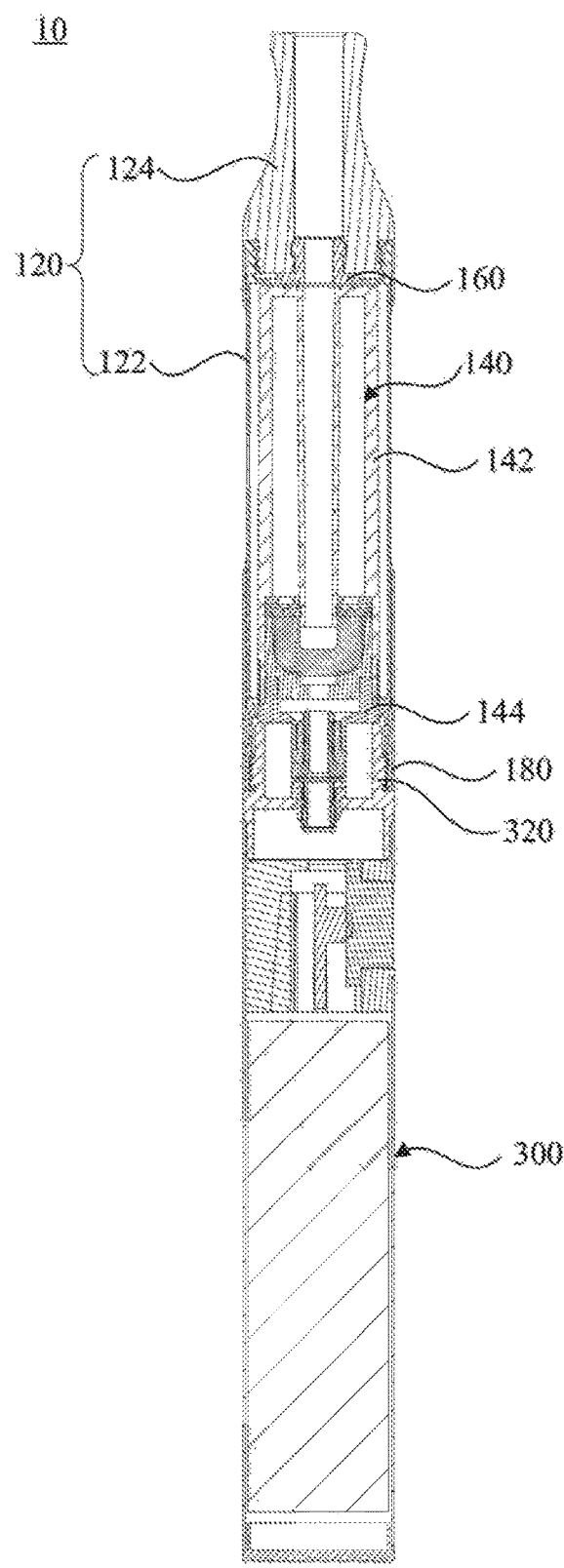
FIG. 3 is a cross-sectional view of the electronic cigarette of FIG. 1.
Figure 4:
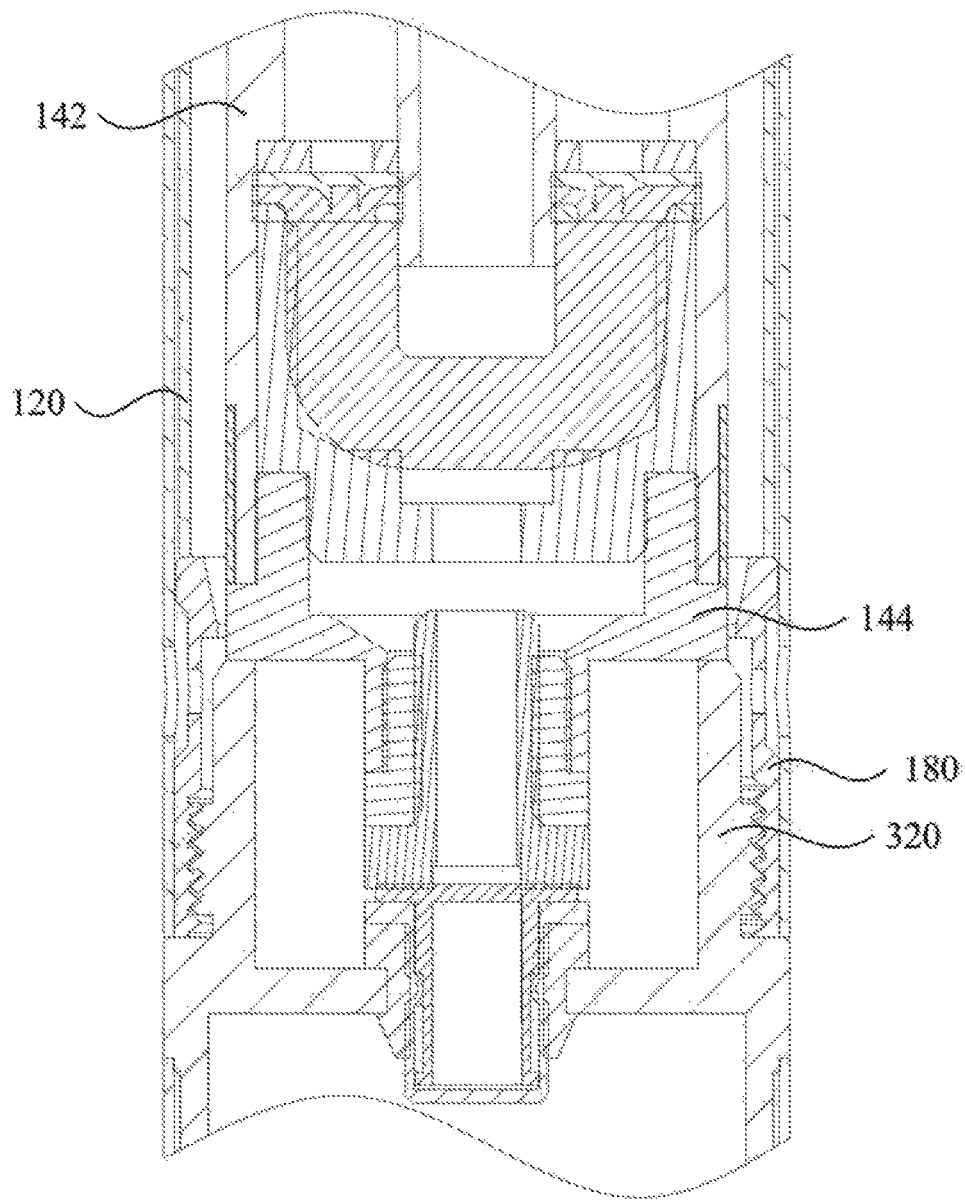
FIG. 4 is an partial, enlarged view of the electronic cigarette of FIG. 3.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring to FIG. 1 and FIG. 2, an electronic cigarette 10 according to an embodiment includes an atomizing assembly 100 and a power supply assembly 300, which are removably connected to each other. Referring to FIG. 3, the atomizing assembly 100 includes a housing 120 and an atomizer 140 located in the housing 120. Referring to FIG. 4, the power supply assembly 300 includes a first connecting portion 320 facing the atomizer 140. The housing 120 is provided with an abutment portion 160 therein to abut against the atomizer 140. The housing 120 is provided with a second connecting portion 180 on an end thereof facing the power supply assembly 300. The second connecting portion 180 is removably connected to the first connecting portion 320, e.g., the first connecting portion 320 is threadedly connected to the first connecting portion 320. The atomizer 140 includes a reservoir 142 and an atomizing element connected to the reservoir 142, and the atomizer 140 is provided with a third connecting portion 144 on an end thereof facing the power supply assembly 300. When the first correcting portion 320 is fixedly connected to the second connecting portion 180, the abutment portion 160 abuts against the atomizer 140, such that the third connecting portion 144 abuts against the first connecting portion 320, thereby fixing the atomizer 140 in the housing 120.

During assembly of the foregoing electronic cigarette 10, the atomizer 140 is firstly received in the housing 120, the power supply assembly 300 is then connected the housing 120, the first connecting portion 320 is connected to the second connecting portion 180, the abutment portion 160 abuts against the atomizer 140, such that the third connecting portion 144 abuts against the first connecting portion 320, thereby fixing the atomizer 140 in the housing 120. The electronic cigarette 10 has a simple structure, easy assembly and low cost.

In one embodiment, when the first connecting portion 320 is fixedly connected to the second connecting portion 180, the atomizer 140 is compressed between the abutment portion 160 and the power supply assembly 300. When the first connecting portion 320 is disengaged from the second connecting portion 180, the atomizer 140 can be removed from the housing 120. The reservoir 142 of the atomizer 140 is used to store liquid, especially tobacco flavored e-liquid. When the liquid is exhausted, the user can easily remove or reload the atomizer 140. Since the atomizer 140 can be removed and reload as a whole, a convenient and sanitary replacement of the atomizer 140 can be achieved.

Figure 5:
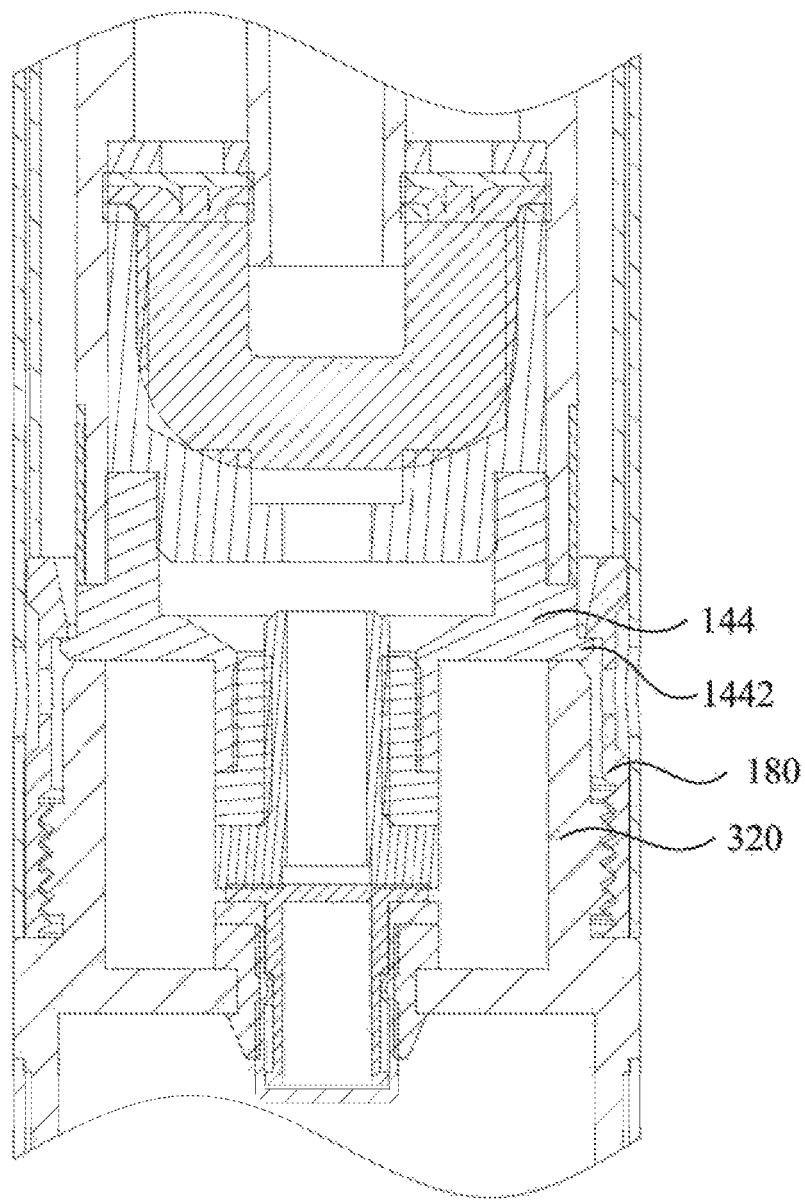
FIG. 5 is an partial enlarged view of the electronic cigarette according to another embodiment.

In one embodiment the third connecting portion 144 serves also as a negative electrode of the atomizing assembly 100, and the first connecting portion 320 serves also as a negative electrode of the power supply assembly 300. When the first connecting portion 320 is fixedly connected to the second connecting portion 180, an end of the first connecting portion 320 abuts against the third connecting portion 144. In the illustrated embodiment, since the third connecting portion 144 can be electrically coupled to the first connection portion 320 directly, there is no need to provide a boss for the third connecting portion 144 for electrically coupling to the second connecting portion 180. Referring to FIG. 5, in alternative embodiments, the third connecting portion 144 is provided with a boss 1442 configured for electrically connecting the second connecting portion 180. The second connecting portion 180 is electrically coupled to the first connecting portion 320. Serving as an auxiliary electrical coupling position, the boss 1442 can improve the reliability of the electrical coupling between the third connecting portion 144 and the first connecting portion 320.

Figure 6:
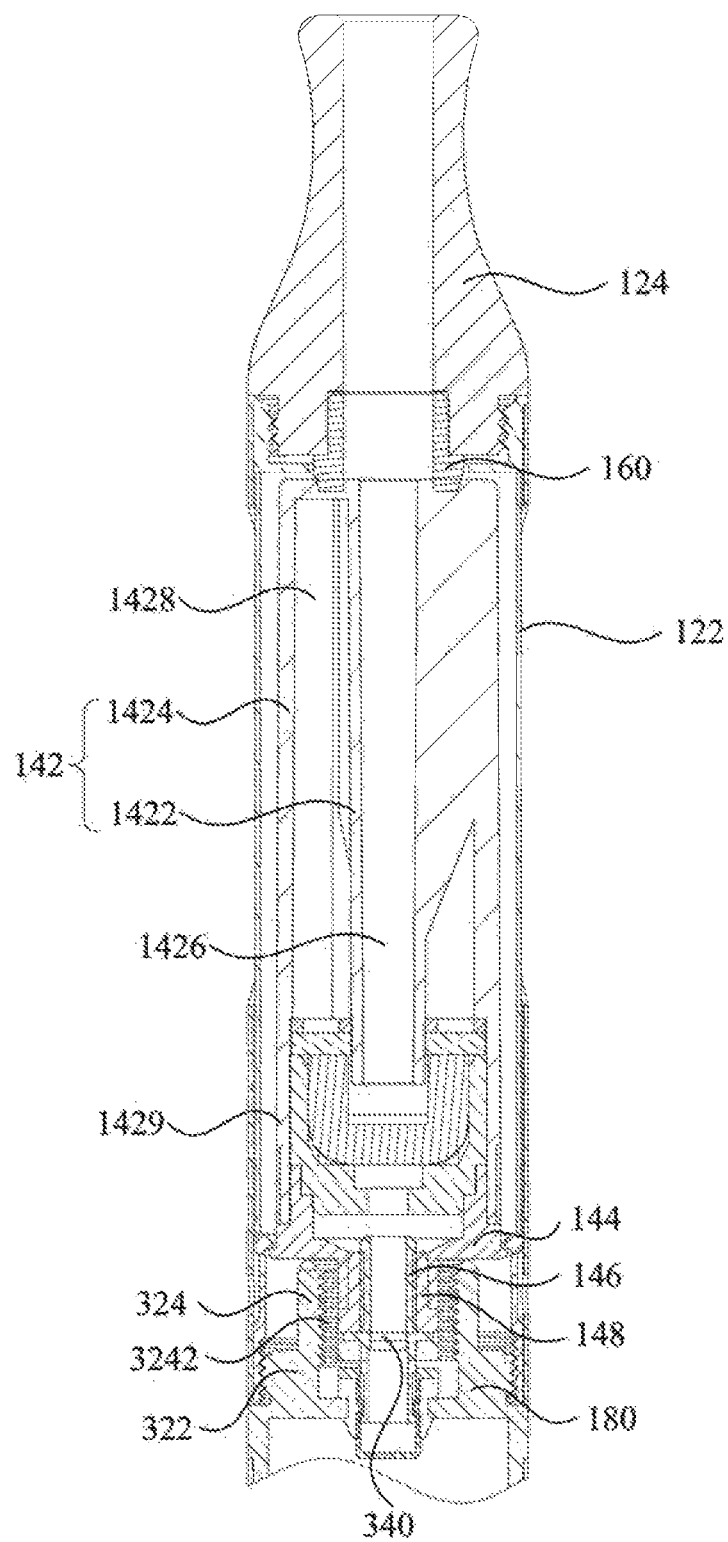
FIG. 6 is an partial, enlarged view of the electronic cigarette according to another embodiment.

Referring to FIG. 6, in alternative embodiments, the third connecting portion 144 serves also as a negative electrode and defines an air inlet, the third connecting portion 144 is electrically coupled to a negative electrode of the atomizing element. The atomizer 140 bather includes a positive electrode connecting member 146 and an insulating sleeve 148. The positive electrode connecting member 146 is located at the air inlet. The positive electrode connecting member 146 is electrically coupled to a positive electrode of the atomizing element. The insulating sleeve 148 is sleeved on the positive electrode connecting member 146, and the insulating sleeve 148 is located between the third connecting portion 144 and the positive electrode connecting member 146, such that the third connecting portion 144 is insulated from the positive electrode connecting member 146.

Figure 7:
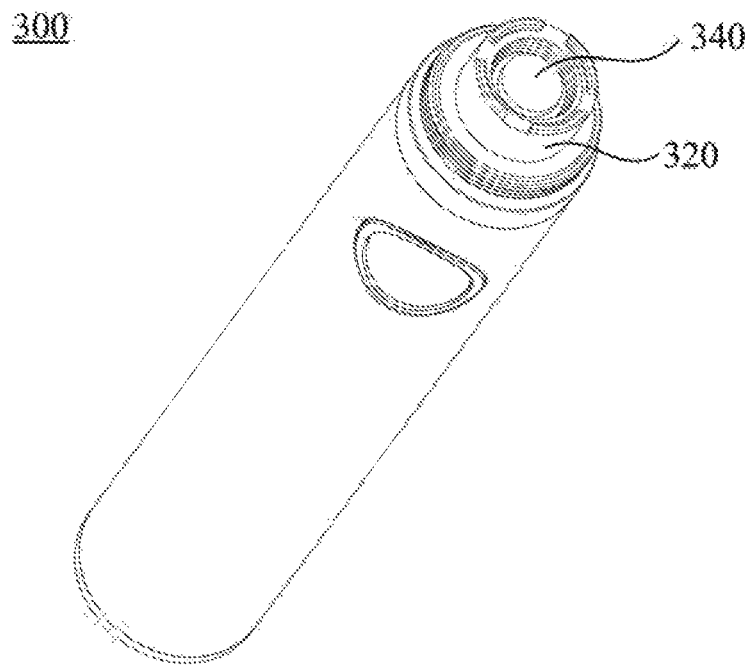
FIG. 7 is a perspective view of a power supply assembly of the electronic cigarette of FIG. 6.
Figure 8:
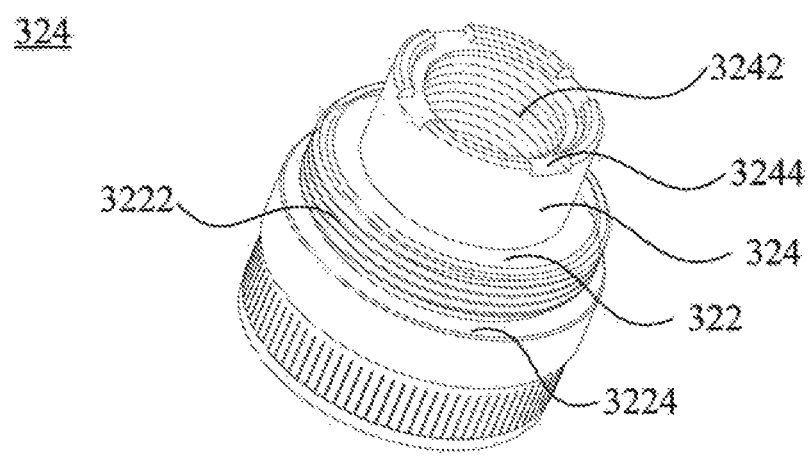
FIG. 8 is a perspective view of a first connecting portion of an atomizer of the electronic cigarette of FIG. 6.

Referring also to FIG. 7, the power supply assembly 300 further includes a positive electrode contact boss 340. The first connecting portion 320 serves also as a negative electrode and surrounds an outside of the positive electrode contact boss 340. Referring also to FIG. 8, the first connecting portion 320 can include a first main body 322 and a tubular portion 324, which are fixedly connected. The positive electrode contact boss 340 is insulated from the first main body 322. In one embodiment, the tubular portion 324 is provided with a connecting thread 3242 for connecting to a charging device.

When the first connecting portion 320 is fixedly connected to the second connecting portion 180, the tubular portion 324 is sleeved on both of the positive electrode connecting member 146 and the insulating sleeve 148, an end of the tubular portion 324 abuts against, the third connecting portion 144, and the positive electrode connecting member 146 abuts against the positive electrode contact boss 340. At this time, the positive electrode of the atomizing assembly 100 is electrically coupled to the positive electrode of the power supply assembly 300, the negative electrode of the atomizing assembly 100 is electrically coupled to the negative electrode of the supply assembly 300, while the positive electrode is insulated from the negative electrode. The foregoing connection has a simple structure, easy assembly, and a good reliability.

In one embodiment, in order to ensure smooth ventilation, an end of the tubular portion 324, which is used to abut against the third connecting portion 144, defines a ventilation groove 3244 communicating an inside and an outside of the tubular portion 324. In alternative embodiments, as a substitute of the ventilation groove 3244, the tubular portion 324 may define a ventilation vent thereon communicating an inside and an outside of the tubular portion 324. In alternative embodiments, the ventilation groove 3244 and the ventilation vent can both be provided.

Figure 9:
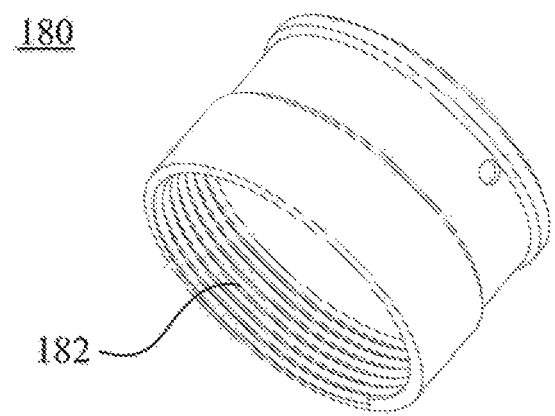
FIG. 9 is a perspective view of a second connecting portion of an atomizer of the electronic cigarette of FIG. 6.

Referring to FIG. 9, in one embodiment, the second connecting portion 180 has a tubular shape and is provided with an internal thread 182. The first main body 322 is provided with an external thread 3222 fitting with the internal thread 182, the second connecting portion 180 is threadedly connected to the first main body 322. In addition, in one embodiment, the first main body 322 is provided with a stepped portion 3224, which is adjacent to the external thread 3222. When the first connecting portion 320 is fixedly connected to the second connecting portion 180, the second connecting portion 180 abuts against the stepped portion 3224. The abutment between the second connecting portion 180 and the stepped portion 3224 has a positioning function, so as to avoid the poor contact of the circuit due to dislocation caused by the rotation.

Figure 10:
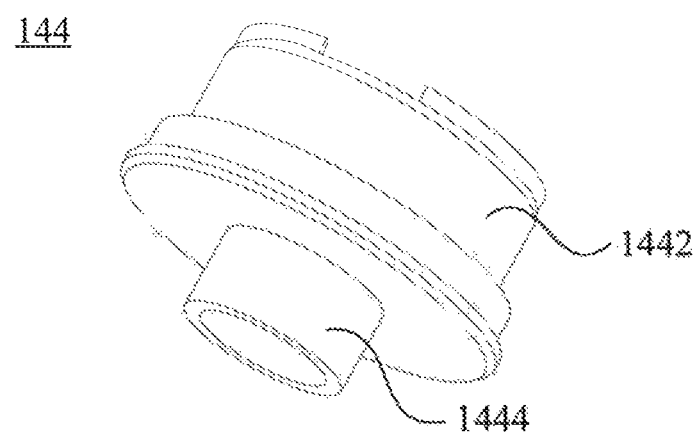
FIG. 10 is a perspective view of a third connecting portion of an atomizer of the electronic cigarette of FIG. 6.

Referring also to FIG. 10, additionally, in one embodiment, the third connecting portion 144 includes a third main body 1442 and a connecting tube 1444 which are fixedly connected. The connecting tube 1444 is located at the air inlet. The positive electrode connecting member 146 is at least partially located in the connecting tube 1444, such that the positive electrode connecting member 146 is firmly connected to the third connecting portion 144.

Figure 11:
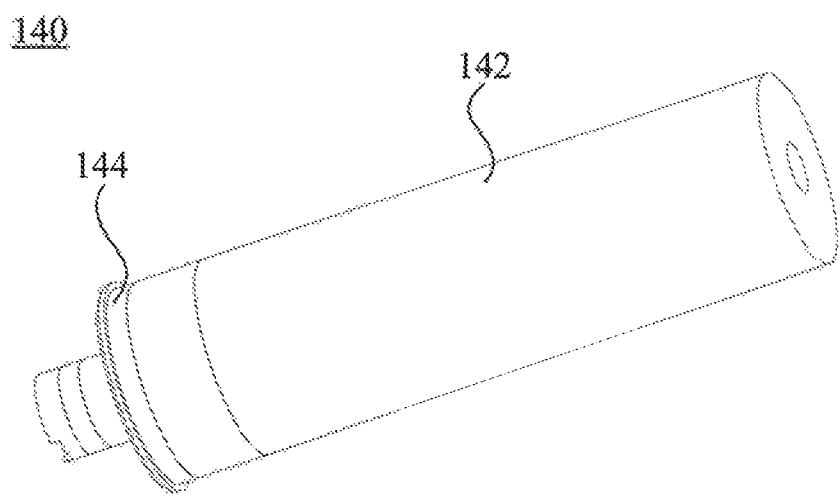
FIG. 11 is a perspective view of an atomizer of the electronic cigarette according to another embodiment.
Figure 12:
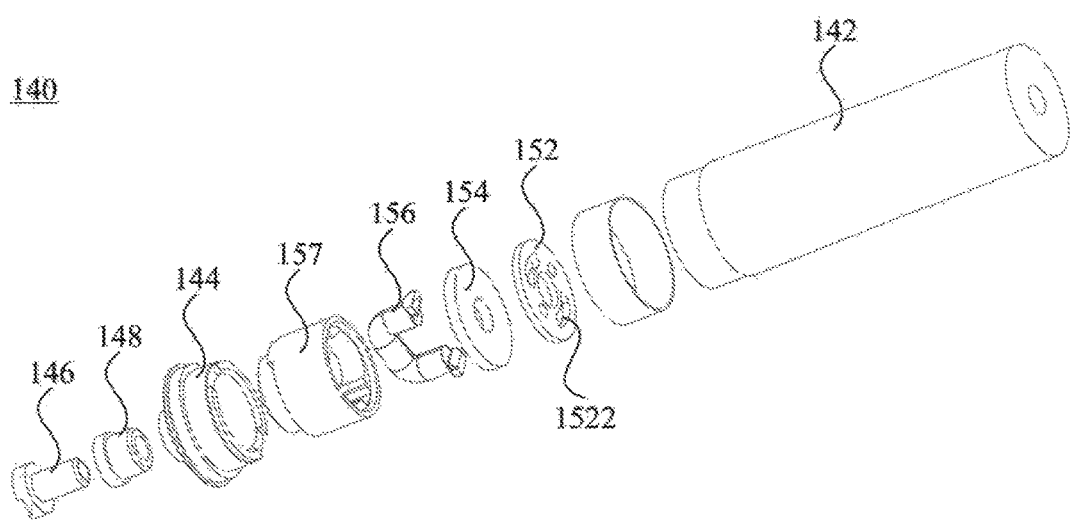
FIG. 12 is an exploded view of the atomizer of the electronic cigarette of FIG. 11.
Figure 13:
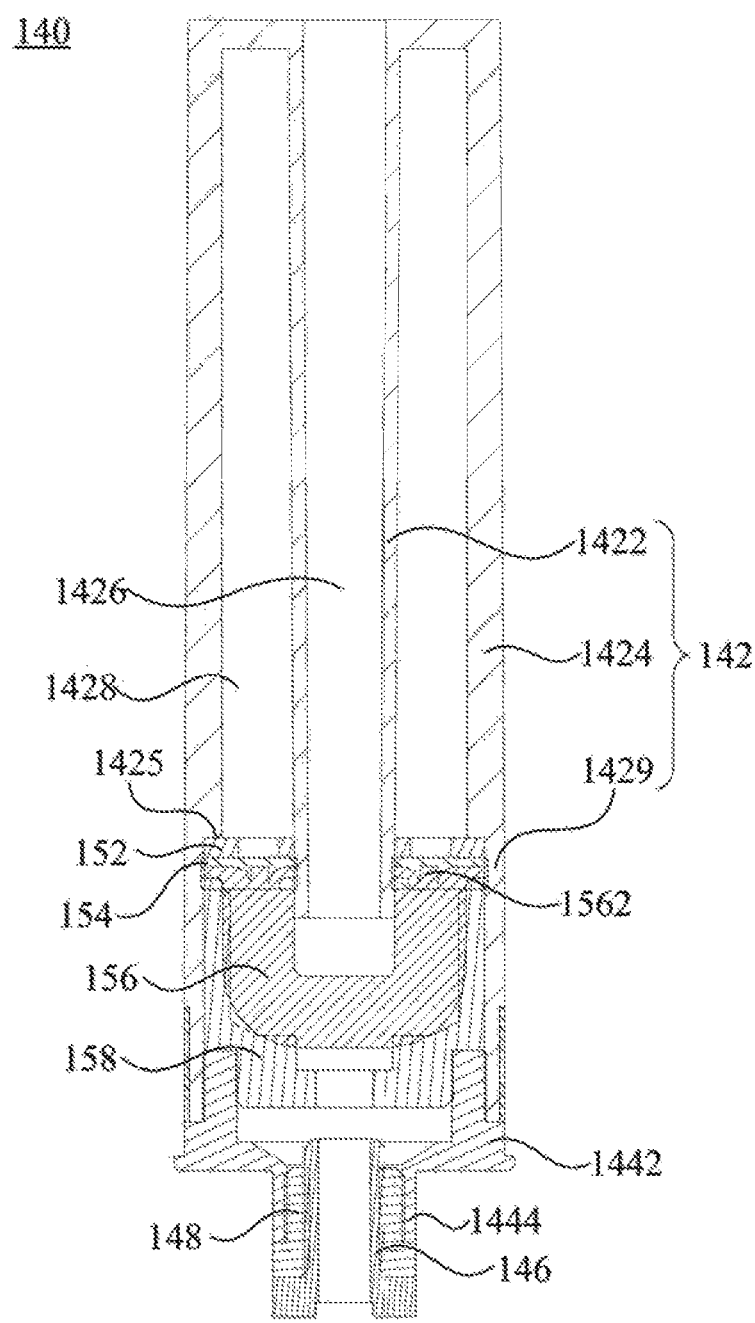
FIG. 13 is a cross-sectional view of the atomizer of the electronic cigarette of FIG. 11.

Referring also to FIG. 11 to FIG. 13, in one embodiment, the atomizer 140 further includes a spacer 152, a liquid storage layer 134, and a liquid conduction cord 156. The reservoir 142 includes an inner tube 1422 and an outer tube 1424, the inner tube 1422 is at least partially received in the outer tube 1424. The inner tube 1422 defines an airflow channel 1426 therein. The inner tube 1422 and the outer tube 1424 cooperatively form a liquid storage chamber 1428 therebetween for restoring liquid. The spacer 152 and the liquid storage layer 154 are sleeved on the inner tube 1422, the spacer 152 is positioned between the liquid storage chamber 1428 and the liquid storage layer 154. A side of the liquid storage layer 154 abuts against the spacer 152. The spacer 152 defines a liquid-conducting hole 1522 communicating the liquid storage chamber 1428 and the liquid storage layer 154, the liquid storage layer 154 is configured to absorb and store liquid in die liquid storage chamber 1428. Another side of the liquid storage layer 154 abuts against the liquid conduction cord 156. The liquid conduction cord 156 is configured to absorb the liquid in the liquid storage layer 154. The atomizing element is fixedly connected to the liquid conduction cord 156, and the atomizing element is configured to atomize the liquid in the liquid conduction cord 156.

The liquid in the liquid storage chamber 1428 is in contact with the liquid storage layer 154 via the liquid-conducting hole 1522 of the spacer 152, then the liquid is absorbed by the liquid storage layer 154. The liquid conduction cord 156 absorbs the liquid in the liquid storage layer 154, such that the atomizing element can atomize the liquid in the liquid conduction cord 156. The spacer 152 has a high liquid passing rate, which can be roughly controlled by the configuration of the number and the diameter of the liquid-conducting hole 1522. The liquid storage layer 154 has a low liquid passing rate, and the passing amount of the liquid can further be precisely controlled by the liquid storage layer 154. Due to the collective effect of the spacer 152 and the liquid storage layer 154, the control accuracy of the amount of the liquid in the liquid conduction cord 156 is effectively improved. Since the spacer 152 and the liquid storage layer 154 are both sleeved on the inner tube 1422, the assembly of the spacer 152 and the liquid storage layer 154 is based on the inner tube 1422, thus facilitating the assembly. The spacer 152 has an inexpensive sheet-like structure, which reduces the production cost.

Since the spacer 152 and the liquid storage layer 154 are both sleeved on the inner tube 1422, the assembly of the spacer 152 and the liquid storage layer 154 is based on the inner tube 1422, thus facilitating the assembly. The spacer 152 can be made of rigid materials, thus further facilitating the assembly. The spacer 152 has a sheet-like structure, in one embodiment, the spacer 152 can be a plastic sheet with holes, which is inexpensive, thus reducing the production cost. The number of the liquid-conducting hole 1522 can be one or more. The shape of the liquid-conducting hole 1522 is best not to be circular, because circular holes tend to form a stable film on its surface if the liquid in the liquid storage chamber 1428 has a large viscosity and surface tension, the film will block the liquid from flowing out. Accordingly, in a preferable embodiment, at least one liquid-conducting hole 1522 has a non-circular shape, which is not easy to from the film, thus ensuring a smooth passing of liquid.

Referring to FIG. 13, in one embodiment, the reservoir 142 further includes an extending tube 1429 connected to an edge of the outer tube 1424 and extending away from the outer tube 1424. The extending tube 1429 defines a receiving cavity therein, the spacer 152 and the liquid storage layer 154 are received in the receiving cavity. The liquid storage layer 154 abuts against an inner side wall of the extending tube 1429, and the liquid storage layer 154 seals a space between the extending tube 1429 and the inner tube 1422. In the illustrated embodiment, the inner tube 1422, the outer tube 1424, and the extending tube 1429 can be integrated formed. The extending tube 1429 has a greater inner diameter than that of the outer tube 1424. A step portion 1425 is formed at a connecting portion between the extending tube 1429 and the outer tube 1424, and the spacer 152 is latched on the step portion 1425. The connection method of the illustrated embodiment makes the assembly of the atomizer 140 more convenient, and the connection is stable and reliable. In one embodiment, the liquid storage layer 154 abuts against the inner sidewall of the extending tube 1429, and the liquid storage layer 154 seals the space between the extending tube 1429 and the inner tube 1422. The liquid storage layer 154 can prevent the liquid from running out of the liquid storage chamber 1428, such that it acts as a seal to ensure sealing between the liquid storage chamber 1428 and the airflow channel 1426.

Figure 14:
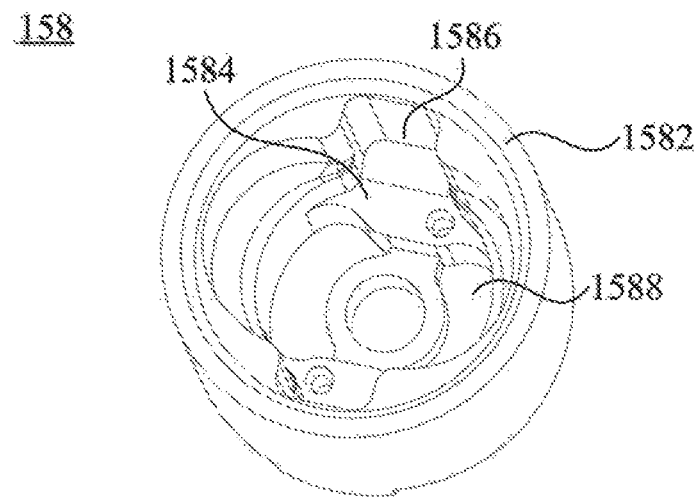
FIG. 14 is a perspective view of an atomizing base of the atomizer of the electronic cigarette of FIG. 11.

Referring also to FIG. 14, in one embodiment, the atomizer 140 further includes an atomizing base 158 defining an atomization chamber therein. One end of the atomizing base 158 has an opening, the other end of the atomizing base 158 defines a through hole communicating the atomization chamber and an outside of the atomizing base 158. The liquid conduction cord 156 is located in the atomization chamber, and an edge of the end of the atomizing base 158 having the opening abuts against the liquid storage layer 154. The atomizing base 158 provides a sealed space for atomization, air can enter the atomization chamber via the through hole, the atomized liquid can enter the airflow channel 1426 and is inhaled by the user.

The atomizing element includes a wire (not shown), the atomizing element is located in the atomization chamber, and the wire requires to extend through the atomizing base 158. In one embodiment, the atomizing base 158 is made of resilient materials, such as silica gel. The atomizing base 158 can be provided with a wire hole which may be formed by wire extending through a blind bole. After the wire extends through the atomizing base 158, the atomizing base 158 can utilize its own elasticity to seal the periphery of the wire, so as to prevent the liquid from flowing out of the atomization chamber along the wire.

In addition, the atomizing base 158 can includes a sidewall 1582 and a bottom surface 1584. The sidewall 1582 has a tubular shape with a short length, the bottom surface 1584 is connected to one end of the sidewall 1582. The blind hole and the through hole can both be provided on the bottom surface 1584. In one embodiment, the sidewall 1582 defines a groove 1586 to accommodate the liquid conduction cord 156, such that the liquid conduction cord 156 can be precisely positioned and is less likely to be moved. In one embodiment, the bottom surface 1584 defines another groove 1588 to receive the liquid dripped by the liquid conduction cord 156, such that the liquid dropping from the liquid conduction cord 156 is not easily to be accumulated in the surrounding of the wire, thus further preventing the liquid from flowing out of the atomization chamber along the cord.

Referring also to FIG. 13, in one embodiment the liquid conduction cord 156 includes a plurality of filaments 1562, ends of the plurality of filaments 1562 are split. Some parts of ends of the plurality of filaments 1562 abut against the liquid storage layer 154, and the rest of ends of the plurality of filaments 1562 are sandwiched between the atomizing base 158 and the liquid storage layer 154. The above-mentioned splitting of the plurality of filaments 1562 can be formed by dispersing the tip of the liquid conduction cord 156. The split filaments 1562 can increase the contact area between the filaments 1562 and the liquid storage layer 154, thereby increasing the flowing rate of the liquid between the filaments 1562 and the liquid storage layer 154.

The liquid conduction cord 156 generally has two ends, and the two ends are located at opposing sides of the inner tube 1422. Furthermore, in one embodiment, some parts of ends of the plurality of filaments 1562 abut against the liquid storage layer 154, while the rest of ends of the plurality of filaments 1562 are sandwiched between the atomizing base 158 and the liquid storage layer 154, thus ensuring the stability of the liquid conduction cord 156 and preventing the liquid conduction cord 156 from being disengaged from the liquid storage layer 154 due to gravity or the like. Moreover, at the splitting position of the plurality of filaments 1562, the length of the filament 1562 whose end is in contact with the liquid storage layer 154 may be less than the length of the filament 1562 which is sandwiched between the atomizing base 158 and the liquid storage layer 154. The sandwiched filament 1562 has a greater length, such that a sufficient contact area between the filament 1562 and the atomizing base 158 and the liquid storage layer 154 can be ensured, thus increasing the reliability of clamping. The filament 1562 which abuts against the liquid storage layer 154 has a less length, thus it is possible to prevent the filaments 1562 from accumulating at a location contacting the liquid storage layer 154, for the accumulating may cause squeezing between the filaments 1562 and blocking of the liquid conduction. Meanwhile, the top end of the filaments 1562 is in contact with the liquid storage layer 154, thus further ensuring the liquid conduction rate. It should be noted that, FIG. 13 only shows a schematic view of the splitting state of the filaments 1562, the number of the filaments 1562 is actually greater than that shown in FIG. 13, and the filaments 1562 may be intertwined with each other.

Figure 15:
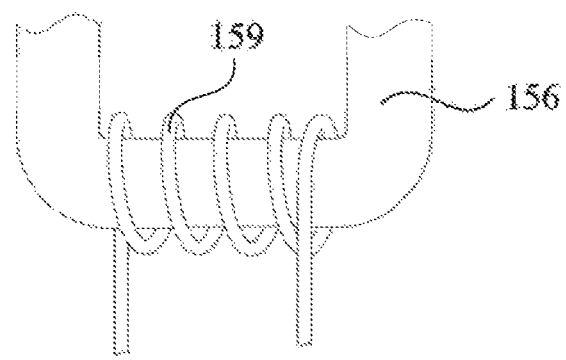
FIG. 15 is a schematic view of a liquid conduction cord and an atomizing element of the atomizer of the electronic cigarette of FIG. 11.

Referring to FIG. 15, the atomizing element can include a heating wire 159, which is wound on a middle portion of the liquid conduction cord 156. The inner tube 1422 defines an opening thereon communicating the airflow channel 1426 and the atomization chamber. The through hole is aligned with the opening on the inner tube 1422, and the heating wire 159 is located between the through hole and the opening on the inner tube 1422. The heating wire 159 is configured at such position that the atomized liquid can be taken away by the airflow directly and not easy to be condensed on the inner wall of the atomization cavity. In one embodiment, a distance between the heating wire 159 and the inner tube 1422 is greater than 2 mm. The inner tube 1422 is generally made of plastic, which may be deformed in case of heating. Since the distance between the heating wire 159 and the inner tube 1422 is greater than 2 mm, it can be prevented that the inner tube 1422 is heated and deformed by the heating wire 159.

Referring to FIG. 3 and FIG. 6, in one embodiment, the housing 120 includes a pipe 122 and a mouthpiece 124 connected to an end of the pipe 122. The abutment portion 160 is located at an inner side wall of the pipe 122, or the abutment portion 160 is located at the mouthpiece 124. The position of the abutment portion 160 can be relatively flexible, as long as the abutment portion 160 can abut against the atomizer 140 after the atomizer 140 is received in the pipe 122. In one embodiment the abutment portion 160 is made of a resilient material, such as silica gel. The abutment portion 160 and the third connecting portion 144 are located at both ends of the atomizer 140. When the third connecting portion 144 abuts against the first connecting portion 220, the atomizer 140 can be clamped and fixed by the abutment portion 160 and the first connecting portion 320. Since the abutment portion is elastic, the third connecting portion 144 and the first connecting portion 320 can maintain a stable abutting condition, thus improving the reliability of electrical coupling between the third connecting portion 144 and the first connecting portion 320.

Although the respective embodiments have been described one by one, it shall be appreciated that the respective embodiments will not be isolated. Those skilled in the art can apparently appreciate upon reading the disclosure of this application that the respective technical features involved in the respective embodiments can be combined arbitrarily between the respective embodiments as long as they have no collision with each other.

The foregoing descriptions are merely specific embodiments of the present invention, but are not intended to limit the protection scope of the present invention. Any variation or replacement readily figured out by a person skilled in the art within the technical scope disclosed in the present invention shall all fall within the protection scope of the present invention. Therefore, the protection scope of the present invention shall be subject to the protection scope of the appended claims.

What is claimed is:

1. An electronic cigarette, comprising:
   an atomizing assembly comprising a housing and an atomizer removably located in the housing,
   the housing having an abutment portion, the atomizer comprising a reservoir and an atomizing element connected to the reservoir; and
   a power supply assembly removably connected to the atomizing assembly, the power supply assembly comprising a first connecting portion facing the atomizing assembly;
   wherein the housing is provided with a second connecting portion on an end thereof facing the power supply assembly, the second connecting portion being removably connected to the first connecting portion;
   wherein the atomizer is provided with a third connecting portion on an end thereof facing the power supply assembly; and
   wherein when the first connecting portion is fixedly connected to the second connecting portion, the abutment portion abuts against the atomizer, such that the third connecting portion abuts against the first connecting portion.

2. The electronic cigarette according to claim 1, wherein the third connecting portion serves as a negative electrode of the atomizing assembly, and the first connecting portion serves as a negative electrode of the power supply assembly.

3. The electronic cigarette according to claim 1, wherein the third connecting portion defines an air inlet, the third connecting portion is electrically coupled to a negative electrode of the atomizing element; wherein the atomizer further comprises a positive electrode connecting member and an insulating sleeve, the positive electrode connecting member being located at the air inlet, the positive electrode connecting member being electrically coupled to a positive electrode of the atomizing element, the insulating sleeve being sleeved on the positive electrode connecting member, and the insulating sleeve being located between the third connecting portion and the positive electrode connecting member, such that the third connecting portion is insulated from the positive electrode connecting member;

wherein the first connecting portion serves as a negative electrode of the power supply assembly, the first connecting portion comprising a first main body and a tubular portion which are fixedly connected; wherein the power supply assembly further comprises a positive electrode contact boss, the positive electrode contact boss is insulated from the first main body; and wherein when the first connecting portion is fixedly connected to the second connecting portion, the tubular portion is sleeved on both of the positive electrode connecting member and the insulating sleeve, an end of the tubular portion abuts against the third connecting portion, and the positive electrode connecting member abuts against the positive electrode contact boss.

4. The electronic cigarette according to claim 3, wherein the third connecting portion comprises a third main body and a connecting tube which are fixedly connected, the connecting tube is located at the air inlet, the positive electrode connecting member is at least partially located in the connecting tube.

5. The electronic cigarette according to claim 3, wherein the tubular portion is provided with a connecting thread for connecting to a charging device.

6. The electronic cigarette according to claim 3, wherein the tubular portion defines a ventilation vent communicating an inside and an outside of the tubular portion.

7. The electronic cigarette according to claim 3, wherein an end of the tubular portion abutting against the third connecting portion defines a ventilation groove communicating an inside and an outside of the tubular portion.

8. The electronic cigarette according to claim 3, wherein the second connecting portion has a tubular shape, the second connecting portion is provided with an internal thread, the first main body is provided with an external thread fitting with the internal thread, the second connecting portion is threadedly connected to the first main body.

9. The electronic cigarette according to claim 8, wherein the first main body is provided with a stepped portion adjacent to the external thread; when the first connecting portion is fixedly connected to the second connecting portion, the second connecting portion abuts against the stepped portion.

10. The electronic cigarette according to claim 1, wherein when the first connecting portion is fixedly connected to the second connecting portion, the atomizer is compressed between the abutment portion and the power supply assembly; when the first connecting portion is disengaged from the second connecting portion, the atomizer is removable from the housing.

11. The electronic cigarette according to claim 10, wherein the atomizer further comprises a spacer, a liquid storage layer, and a liquid conduction cord;

wherein the reservoir comprises an inner tube and an outer tube, the inner tube being at least partially received in the outer tube, the inner tube defining an airflow channel therein, and wherein the inner tube and the outer tube cooperatively form a liquid storage chamber therebetween for restoring liquid;

wherein the spacer and the liquid storage layer are sleeved on the inner tube, the spacer being positioned between the liquid storage chamber and the liquid storage layer, and wherein a side of the liquid storage layer abuts against the spacer;

wherein spacer defines a liquid-conducting hole communicating the liquid storage chamber and the liquid storage layer, the liquid storage layer being configured to absorb and store liquid in the liquid storage chamber;

wherein another side of the liquid storage layer abuts against the liquid conduction cord, the liquid conduction cord being configured to absorb the liquid in the liquid storage layer; and wherein the atomizing element is fixedly connected to the liquid conduction cord, the atomizing element being configured to atomize the liquid in the liquid conduction cord.

12. The electronic cigarette according to claim 11, wherein the reservoir further comprises an extending tube connected to an edge of the outer tube and extending away from the outer tube, the extending tube defines a receiving cavity therein, the spacer and the liquid storage layer are received in the receiving cavity; the liquid storage layer abuts against an inner sidewall of the extending tube, a space between the extending tube and the inner tube is sealed by the liquid storage layer.

13. The electronic cigarette according to claim 12, wherein the atomizer further comprises an atomizing base defining an atomization chamber therein, the atomizing base has an opening at an end thereof, the atomizing base defines a through hole at the other end thereof communicating the atomization chamber and an outside of the atomizing base, the liquid conduction cord is located in the atomization chamber, and an edge of the end of the atomizing base having the opening abuts against the liquid storage layer.

14. The electronic cigarette according to claim 13, wherein the liquid conduction cord comprises a plurality of filaments, ends of the plurality of filaments are split; part of ends of the plurality of filaments abut against the liquid storage layer, and the rest of ends of the plurality of filaments are sandwiched between the atomizing base and the liquid storage layer.

15. The electronic cigarette according to claim 1, wherein the housing comprises a pipe and a mouthpiece connected to an end of the pipe, the abutment portion is located at an inner sidewall of the pipe, or the abutment portion is located at the mouthpiece.

16. The electronic cigarette according to claim 1, wherein the abutment portion is made of a resilient material.

17. An electronic cigarette, comprising:

an atomizing assembly comprising a housing and an atomizer removably located in the housing, the housing having an abutment portion and the atomizer comprising a reservoir and an atomizing element connected to the reservoir; and a power supply assembly connected to the atomizing assembly, the power supply assembly comprising a first connecting portion facing the atomizing assembly;

wherein the housing is provided with a second connecting portion on an end thereof facing the power supply assembly;

wherein the second connecting portion is removably connected to the first connecting portion;

wherein the atomizer is provided with a third connecting portion on an end thereof facing the power supply assembly; and wherein when the first connecting portion is fixedly connected to the second connecting portion, the abutment portion abuts against the atomizer, such that the third connecting portion abuts against the first connecting portion.

18. The electronic cigarette according to claim 17, wherein the third connecting portion is electrically coupled to a negative electrode of the atomizing element; the atomizer further comprising a positive electrode connecting member coupled to a positive electrode of the atomizing element; wherein the first connecting portion serves as a negative electrode of the power supply assembly, the first connecting portion comprising a first main body; the power supply assembly further comprising a positive electrode contact boss, the positive electrode contact boss being insulated from the first main body; and wherein when the first connecting portion is fixedly connected to the second connecting portion, the positive electrode connecting member abuts against the positive electrode contact boss, and the third connecting portion is electrically coupled to the first connecting portion.

19. The electronic cigarette according to claim 17, wherein the third connecting portion is electrically coupled to a negative electrode of the atomizing element; wherein the atomizer further comprises a positive electrode connecting member and an insulating sleeve, the positive electrode connecting member being electrically coupled to a positive electrode of the atomizing element, the insulating sleeve being sleeved on the positive electrode connecting member, and the insulating sleeve being located between the third connecting portion and the positive electrode connecting member such that the third connecting portion is insulated from the positive electrode connecting member; wherein the first connecting portion serves as a negative electrode of the power supply assembly, the first connecting portion comprising a first main body; wherein the power supply assembly further comprises a positive electrode contact boss, the positive electrode contact boss being insulated from the first main body; and wherein when the first connecting portion is fixedly connected to the second connecting portion, the positive electrode connecting member abuts against the positive electrode contact boss, and the third connecting portion is electrically coupled to the first connecting portion.

20. The electronic cigarette according to claim 17, wherein the third connecting portion is electrically coupled to the first connecting portion by the second connecting portion.

* * * * *